US008758683B2

(12) United States Patent
Lafferty et al.

(10) Patent No.: US 8,758,683 B2
(45) Date of Patent: Jun. 24, 2014

(54) SYSTEM FOR SAMPLING AND TRACKING PLANT MATERIAL

(75) Inventors: William Michael Lafferty, Encinitas, CA (US); Scott Wayne Beaver, San Marcos, CA (US); Charles Wilson Tweedy, San Diego, CA (US); Elizabeth Ann George, La Mesa, CA (US); Walter James Frandsen, Jr., Ramona, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 11/835,986

(22) Filed: Aug. 8, 2007

(65) Prior Publication Data
US 2009/0042180 A1    Feb. 12, 2009

(51) Int. Cl.
*G01N 1/04*    (2006.01)
*G01N 1/28*    (2006.01)
*G01N 35/02*    (2006.01)

(52) U.S. Cl.
CPC .................. *G01N 1/04* (2013.01); *G01N 1/286* (2013.01); *G01N 2001/288* (2013.01); *G01N 35/021* (2013.01)
USPC ....... 422/63; 422/501; 73/864.41; 435/284.1; 435/286.2

(58) Field of Classification Search
USPC .......................................... 422/65
See application file for complete search history.

(56) References Cited

U.S. PATENT DOCUMENTS

| 3,832,140 | A | * | 8/1974 | Lorch et al. ...................... 422/65 |
| 4,039,286 | A | * | 8/1977 | Keller et al. .................... 436/47 |
| 5,595,707 | A | | 1/1997 | Copeland |
| 5,638,170 | A | * | 6/1997 | Trinka et al. .................. 356/244 |
| 5,654,200 | A | | 8/1997 | Copeland |
| 6,150,158 | A | | 11/2000 | Bhide |
| 6,352,861 | B1 | | 3/2002 | Copeland |
| 6,659,338 | B1 | | 12/2003 | Dittmann |
| 6,763,971 | B1 | * | 7/2004 | Tong ............................. 221/151 |
| 6,827,901 | B2 | | 12/2004 | Copeland |
| 7,118,918 | B2 | | 10/2006 | Copeland |
| 7,278,328 | B2 | | 10/2007 | Massaro |
| 7,510,681 | B2 | | 3/2009 | Justin |
| 2002/0164272 | A1 | * | 11/2002 | Harris ........................... 422/101 |
| 2009/0087830 | A1 | | 4/2009 | Dittman |

FOREIGN PATENT DOCUMENTS

FR    2801380    11/1999
JP    07-270429    * 10/1995
JP    7270429    10/1995

* cited by examiner

*Primary Examiner* — P. Kathryn Wright
(74) *Attorney, Agent, or Firm* — R. Kody Jones

(57) ABSTRACT

A system and method for processing, i.e., sampling and tracking, plant material requires the ability to identify each plant in a plurality of plants. Initially, samples are taken from selected plants and are collected in respective storage locations in a magazine. During sampling, the identity of the plant source for each plant sample is stored. Further, the identity of each storage location receiving a plant sample is stored. Subsequently, the samples are transferred from the storage locations and are placed in respective wells of a receiving member for further downstream processing. Again, the identity of each well receiving a plant sample is stored. As a result, a plant sample in a well can be traced back to its plant source.

7 Claims, 2 Drawing Sheets

SYSTEM FOR SAMPLING AND TRACKING PLANT MATERIAL

FIELD OF THE INVENTION

The present invention pertains generally to systems and methods for sampling and tracking plant material from vast numbers of plants. More particularly, the present invention pertains to systems and methods that obtain molecular information from leaf sample material for use in DNA, RNA, proteins or metabolite analysis applied to discovery, marker assisted selection or quality control programs. The present invention is particularly, but not exclusively, useful for obtaining genetic marker information from a vast number of plants to aid in the selection of plants.

BACKGROUND OF THE INVENTION

It is well known that genetic markers can be obtained from DNA and used for a variety of purposes. For example, in the field of plant analysis, the DNA obtained from plant material can be analyzed to generate molecular marker information. In this process, DNA sequence variation can be analyzed to first discover correlations between molecular markers and traits. Then, plants may be selected for desired traits based on molecular marker information. Traits selected through this process may include, without limitation, agronomic traits such as yield, abiotic stress tolerance, biotic stress tolerance, or end user traits such as plant composition, animal nutrition traits, human health, and the like.

For marker assisted breeding, seeds of plants with a desired trait are planted in soil either in a greenhouse or in a field. Plant tissue (i.e. leaf) is then harvested from the plants for preparation of DNA once sufficient tissue can be removed from the plants without compromising their viability. Thus, genomic DNA is isolated for further processing to find specific genetic characteristics. In the subsequent processing, these characteristics are linked to traits of interest and are thereby used to predict the presence or absence of the traits of interest in the sampled plants.

As a practical matter, the identification of plants involves complicated procedures that are difficult, if not impossible, to accomplish on-site in the field. The situation becomes further complicated when a large number of plants are involved, such as in a commercial agricultural operation where thousands, or tens of thousands, of different plants are being cultivated in the same field. In such operations, the ability to subsequently identify a particular plant may be of crucial importance.

For a large commercial operation such as mentioned above, several considerations are particularly important. For one, all plants in a field need to be properly identified. For another, these identifications need to be accomplished without undue delay. And, finally, each plant that is identified must be capable of being subsequently found at its field location.

In light of the above, it is an object of the present invention to provide a system and method for processing samples of plant material wherein a particular plant in the field can be subsequently found. Another object of the present invention is to provide a system and method for processing samples of plant material wherein plants can be identified and processed. Still another object of the present invention is to provide a system and method for processing samples of plant material that is easy to implement, is simple to use, and is comparatively cost effective.

SUMMARY OF THE INVENTION

In accordance with the present invention, a system and method for processing, i.e., sampling and tracking, plant material for use in an experiment provide the ability to trace a plant sample to its source plant. In the system, the identity of each individual source plant in a field of such plants must be determinable. To this end, when an experiment is planned, a database of virtual plants is initially created. Specifically, a plurality of virtual plants are identified by an experiment name, e.g., XYZ, and a plant number, e.g., 1 to 999. Also, a number "n" of seeds are sown. After the seeds sprout into plants, each plant is identified either directly or indirectly through the use of a unique machine readable feature. For instance, a unique feature, such as a barcode or a radio frequency identification (RFID) tag may be attached directly to a plant, or attached to a stake at the plant's location. For purposes of the present invention, the unique feature includes the identity of a virtual plant, e.g., XYZ-001. In other words, the sprouted plant is matched to an entry in the experiment database. With the identity of this plant documented, other plants may be identified through their position relative to the documented plant, and likewise matched to a virtual plant in the experiment database, e.g., XYZ-002 through XYZ-999. Alternatively, all plants may be directly identified by a unique feature like a barcode, RFID tag or global positioning system (GPS) coordinates. In any case, each plant is tied to an identity in the database via the unique feature.

After each sprouted plant has been matched with an identity from the experiment database, a sample of plant material can be taken from any selected plant. Preferably, this sample will be in the form of a plug that is taken from a leaf of the plant. For the present invention, as many samples can be taken from the same plant as desired.

In accordance with the present invention, the task of collecting plant material samples is accomplished using a sampling device. For this purpose, a reusable/disposable magazine (cassette) is selectively engaged with the sampling device to collect plant samples. This magazine holds a plurality of storage locations for retaining plant samples. For instance, the storage locations may be comprised of containers or capsules. Alternatively, the storage locations may be defined areas on a surface where samples may be selectively adhered. Regardless of the type of storage location employed, the samples must be captured, confined separately, and identifiable. For purposes of the present invention, the storage locations are positioned on a pathway within each magazine. In operation, the storage locations are advanced along the pathway to a punch position where they individually cooperate with the sampling device, in sequence. More specifically, the sampling device has a punch and die mechanism at the punch position. When activated, this mechanism mechanically cuts a leaf plug from the plant. A storage location at the punch position then captures the severed leaf plug. In certain embodiments, it may be desired that in this operation, a particular storage location receives leaf plugs that have been taken only from the same plant. In other embodiments, however, (e.g. when performing a bulking procedure) a particular storage location can receive leaf plugs from multiple plants. In any event, once a storage location has been filled (e.g. about eight leaf plugs for a typical capsule type of storage location), the magazine will automatically cycle a new storage location to the punch position for cooperation with the sampling device. The operation can then continue until the desired number of storage locations have been appropriately filled. When a sampling procedure is finished, the magazine, and its contents (i.e. the leaf plugs), can be freeze-dried.

It is to be appreciated that in the above described operation, a controller is used to keep track of each plant sample. To this end, whenever a sample is taken from a plant, the identity of the plant is first recorded by reading the unique feature at the plant. If the plant to be sampled does not have a unique feature, then the unique feature of the nearest documented plant is read and its position relative to the plant to be sampled is recorded. Also, each magazine used during sampling is identified through the use of a distinct machine readable feature, such as a barcode or a RFID tag attached to the magazine. Further, each storage location within a magazine is identifiable. Specifically, each magazine includes a register storage location that can be located by the controller. After the register is located, the identity of any storage location can be determined through its position relative to the register. As a result, the controller can record the identity of a selected plant during the sampling procedure, the magazine into which the plant sample is inserted, and the specific storage location that holds the plant sample. Thus, the origin of leaf plugs at a given storage location of the magazine can be traced back to the exact plant or plants from which they were taken. Further, this tracking continues as the plant samples (i.e. leaf plugs) are prepared for additional downstream processing.

After plant sampling is finished for each magazine, the magazine is bundled with other magazines. These magazines may be freeze-dried in order to prolong the viability of the plant samples. Thereafter, the bundled magazines are sent to an on-site location, or to an off-site location, where the plant samples are transferred for additional processing. In accordance with the present invention, this process involves transferring the plant samples from storage locations of the magazine into respective wells of a receiving member such as a continuous conveyor belt or a process tray.

Before the transfer process is actually accomplished, the controller specifies the wells in the receiving member that will receive samples from specific storage locations in the magazine. Thereafter, the controller sequentially aligns the storage locations in the magazine with the specified wells. During conduct of the transfer process, the integrity of the plant samples must be maintained. Stated differently, specific samples should not be mixed with other samples, and should thereby remain undisturbed. Also, the ability to trace each plant sample back to the particular plant from which it was taken must be maintained. In order to allow tracing from a well to the plant source, each receiving member may be identified through the use of a discrete machine readable feature, such as a barcode or a RFID tag attached to the receiving member. Further, each well within a receiving member is identifiable through its position on the receiving member.

As plant samples are transferred from a storage location to a well, a disk from the storage location can also be transferred. Alternatively, the well may be provided with another loose projectile. Subsequently, when the receiving member is shaken, the disk or projectile will act to pulverize the plant plugs, and thereby facilitate preparing the plant sample for the extraction of DNA. This DNA can then be used for the identification of genetic markers.

As envisioned for the present invention, the magazines can be reused or replaced. Specifically, the entire magazine may be reused. In another mode of operation, only the individual storage locations of the magazine are replaced. In another mode, each storage location need not be replaced en toto. Instead, only a disk, that constitutes part of the storage location, is replaced. In still another mode, the entire used magazine is discarded and replaced with a new magazine.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
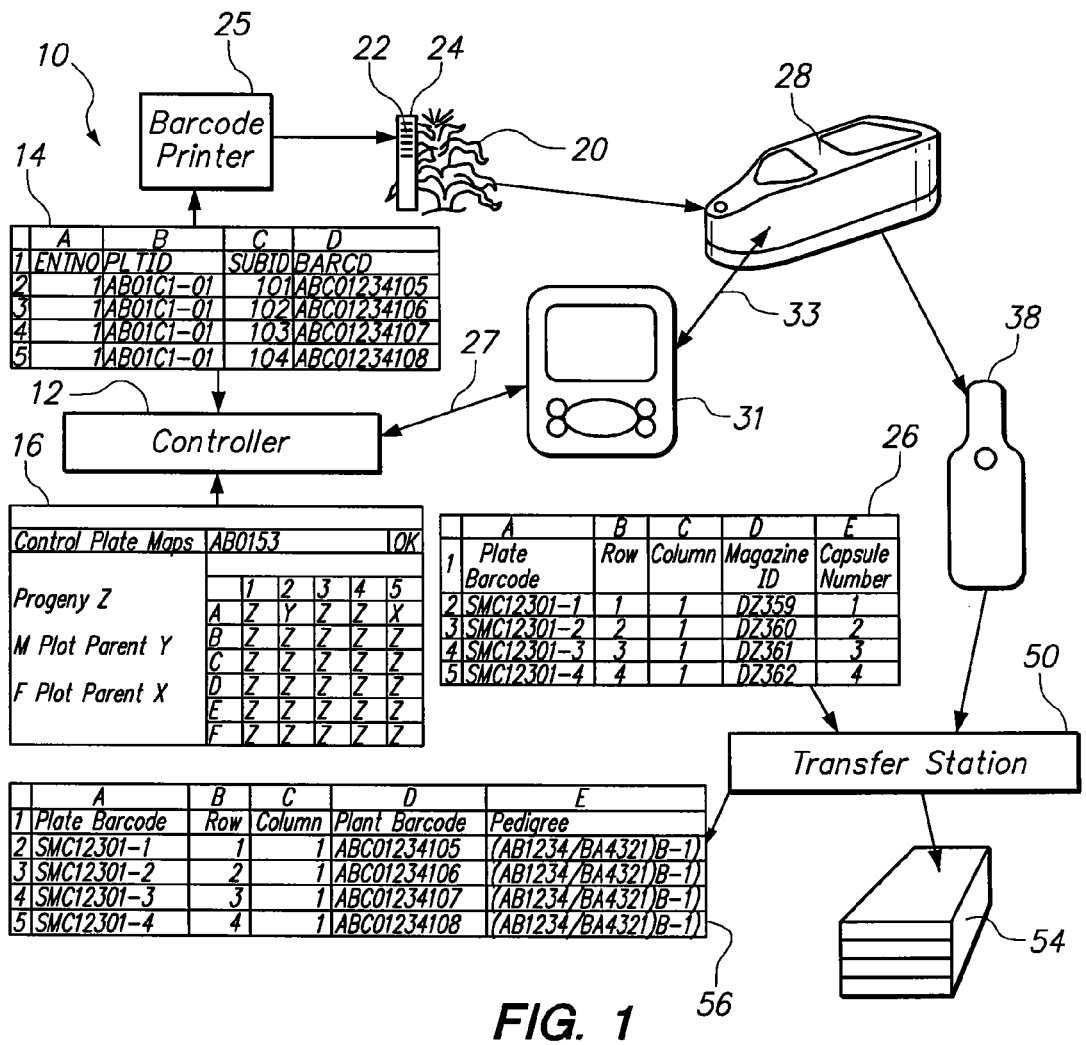
FIG. 1 is a schematic drawing of a system for processing plant samples in accordance with the present invention.
Figure 2:
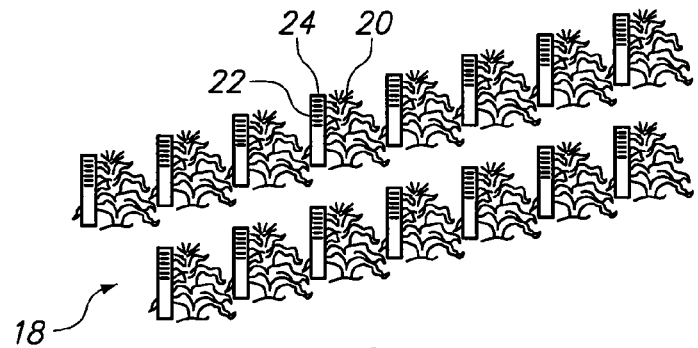
FIG. 2 is a perspective view of a plant field.

Referring initially to FIG. 1, a system in accordance with the present invention is shown and is generally designated 10. As shown, the system 10 includes a controller 12, including process management software, that receives input from two sources. These sources are: a plant database 14 and a data input table 16. Together, these sources (i.e. database 14 and table 16) provide valuable information for monitoring a large number of plants. For example, consider the field that is shown and generally designated 18 in FIG. 2. In order to monitor the plants 20, each plant 20 must be identifiable. For this purpose, inputs to the controller 12 from database 14 allow the user to document the identity of individual plants, such as the plant 20, as well as the identity of other plants 20 in the field 18. Specifically, the database 14 includes a plurality of virtual plants for use in an experiment. For instance, for an experiment XYZ using 500 plants, the database 14 will include virtual plants XYZ-001 through XYZ-500.

Further, the controller 12 will also receive input from the data input table 16 which may include information about a plant's pedigree or the downstream processing intended for samples from the plant 20. For instance, an experiment may require testing of two parent plants 20 and their progeny plants 20. In such a case, the parent plants 20 may be planted in one location while the progeny seeds are planted in another distinct location. Genetic information relating to the parent plants 20 and to the progeny plants 20 may be entered into the data input table 16. Further, instructions for the downstream processing of each type of plant 20 may also be entered into the data input table 16 for use in the handling of samples taken from the plants 20. For instance, the instruction may identify where a sample of the plant 20 should be transferred, how many samples from a plant 20 should be transferred to a particular location, and what testing should be performed on the samples from a plant 20.

In order to identify the plants 20, a unique feature 22 such as a barcode or RFID, for example, is linked to each plant 20. This unique feature 22 may be pre-fabricated or fabricated in physical form in the field 18 and applied to the plant 20 or to a stake 24 placed into the ground adjacent the appropriate plant 20. As shown in FIG. 1, the system 10 includes a device 25 that receives plant information from the plant database 14 and creates the unique features 22 including plant information. In FIG. 1, the creating device 25 is a barcode printer. Depending on the desired procedure, a different unique feature 22 may be made for each plant 20 or for every certain number of plants 20. Thus, each unique feature 22 effectively provides an address for a respective plant 20 or plants 20 in the field 18. As will be discussed below in more detail, this same information on the unique features 22 is also provided for inclusion with subsequently collected field data and is presented in document form as a work-list 26. For purposes of the invention, the work-list 26 includes a list of instructions for the downstream processing of plant samples. Accordingly, the work-list 26 is machine readable, and may be human readable. Typically, the work-list 26 contains information relating to the source of each plant sample, the desired destination of each plant sample, and optimized processing steps involved in moving each plant sample to its desired destination.

For use in the system 10, a sampling device 28 is provided to collect plant material from selected plants 20 in the field 18. During the collection of samples from plants 20, each plant 20 being sampled is first identified by its unique feature 22. Further, it will be appreciated that the sampling data obtained by the sampling device 28 is communicated to the controller 12. In FIG. 1, this communication is performed by a handheld computer 31 with at least a temporary memory such as a "Pocket PC". Specifically, the handheld computer 31 logs the activities of the sampling process and temporarily stores the sampling data for subsequent download to the controller 12 (indicated by arrow 27). It is noted that, while the illustrated system 10 uses a separate handheld computer 31 to provide communication between the sampling device 28 and the controller 12, the sampling device 28 could include memory or data storage that could be downloaded directly to the controller 12 without use of the handheld computer 31 as an intermediary.

As indicated by the double-ended arrow 33, the handheld computer 31 also provides a user interface for establishing various sampling options to be performed by the sampling device 28.

Figure 3:
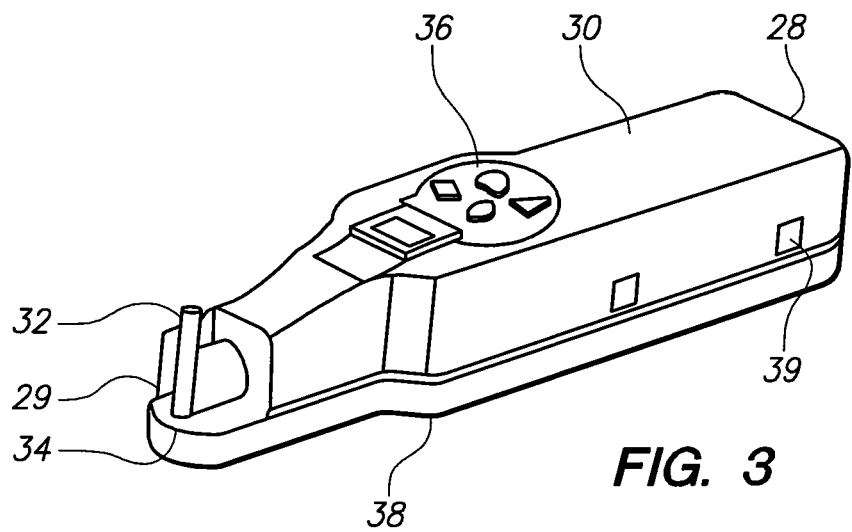
FIG. 3 is a perspective view of a sampling device in accordance with the present invention.

Referring now to FIG. 3, the sampling device 28 is shown to include a housing 30 with a punch 32 and die 34 that are mounted at the front end of the housing 30. A keypad 36 located on the top of the housing 30 is positioned to activate the punch 32 when instructed. Also, the sampling device 28 includes a unit 29, such as a reader or scanner, for retrieving a plant's unique feature 22. In combination, a plant's unique feature 22 and the retrieving unit 29 serve as a means for identifying each plant 20. Thus, whenever, a leaf (not shown) from an identified plant 20 is positioned between the punch 32 and the die 34, and the punch 32 is activated by the keypad 36, a plug (also not shown) will be cut from the leaf. This plug will then be deposited into a magazine 38. As shown in FIG. 3, the magazine 38 is engaged with the sampling device 28. This, however, is a selective engagement as it is intended that the magazine 38 will be removed from the sampling device 28 after the magazine 38 has been filled. The removed magazine 38 can then be replaced on the sampling device 28 by another, similar magazine 38. In order to identify a specific magazine 38 during downstream processing, each magazine 38 is provided with a distinct feature 39 such as a bar code or RFID.

Figure 4:
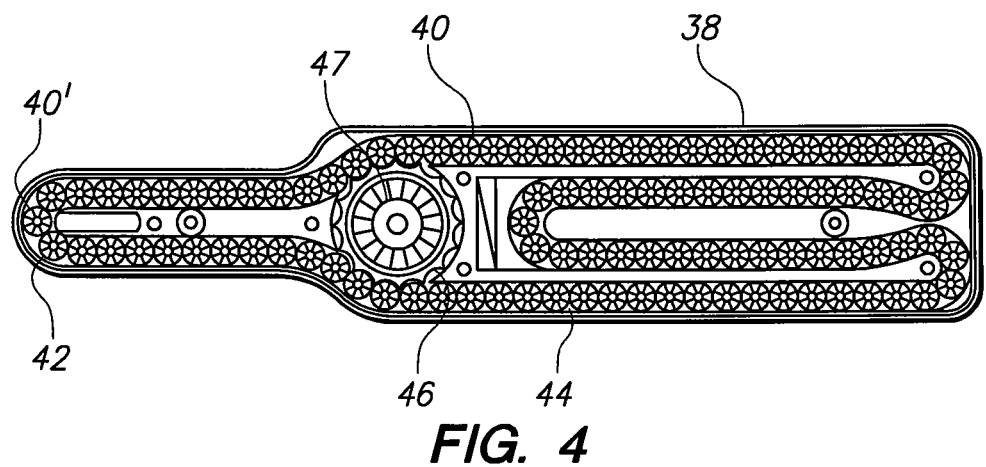
FIG. 4 is a top view of a magazine used for the present invention.

FIG. 4 shows that a magazine 38 for use with the sampling device 28 of the present invention effectively includes ninety-nine storage locations 40 for collecting plant material (i.e. leaf plugs). In the embodiment shown in FIG. 4, the storage locations 40 are capsules that are positioned in the magazine 38, along with a register 42, on a pathway 44. While capsules 40 are illustrated, it is envisioned that the magazine 38 could employ any of a variety of storage locations 40, such as other types of containers or areas which hold plant samples via adhesion or other attractive forces. As shown, the capsules 40 are conveyed along the pathway 44 by a drive mechanism 46 that is mounted on the magazine 38, as shown. The sampling device 28, in turn, operates the drive mechanism 46. Thus, by using the register 42 as a start point, the sampling device 28 is able to align the capsules 40 in an ordered sequence along the pathway 44. The capsules 40 are thereby sequentially presented, in order, as individual capsules 40 at a punch position (shown in FIG. 4 as the position of capsule 40'). Further, the sampling device 28 includes a counter 47 for determining the position of each capsule 40 relative to the register 42. In FIG. 4, it is noted that the capsules 40 are limited to movement on the pathway 44. Further, the illustrated drive mechanism 46 rotates to sequentially engage certain capsules 40 to impart movement to all the capsules 40 along the pathway 44. While these structures cooperate to collect plant samples at the punch position 40', other systems and structures are contemplated for sequentially conveying storage locations 40 along the pathway 44.

It is at the punch position (shown in FIG. 4 by capsule 40') that the punch 32 creates a leaf plug. When a capsule 40 has been filled (e.g. eight leaf plugs), the drive mechanism 46 moves the next-in-line capsule 40 into the punch position. Once the capsules 40 of the magazine 38 have been appropriately filled, the magazine 38 is removed from the sampling device 28. The magazine 38 and its contents (i.e. capsules 40 filled with leaf plugs) may then be freeze-dried. Next, the freeze-dried magazine 38 is bundled with other magazines 38 and prepared for further processing.

Returning to FIG. 1, it is again noted that, during the collection of samples from plants 20, each plant 20 being sampled is first identified by its unique feature 22. Further, it will be appreciated that the sampling data obtained by the sampling device 28 for a magazine 38 is sent to the controller 12 via the handheld computer 31. Specifically, this sampling data will allow the contents (i.e. plant material) of a particular storage location 40 in each magazine 38 to correspond with information on the unique feature 22 of the plant 20 from which the plant material was taken. Stated differently, each storage location 40 is identified with a particular unique feature 22 and with the corresponding plant identity in the database 14. Thus, the work-list 26 that is collated by the controller 12 will include information about the location and the identity of the plant 20 that provided the plant material being held at a particular storage location 40 as well as the identity of the magazine 38 and the storage location 40 in the magazine 38 that holds the plant material. The work-list 26 and the magazine 38 are then both used in a transfer process at the transfer station 50 in FIG. 1.

Figure 5:
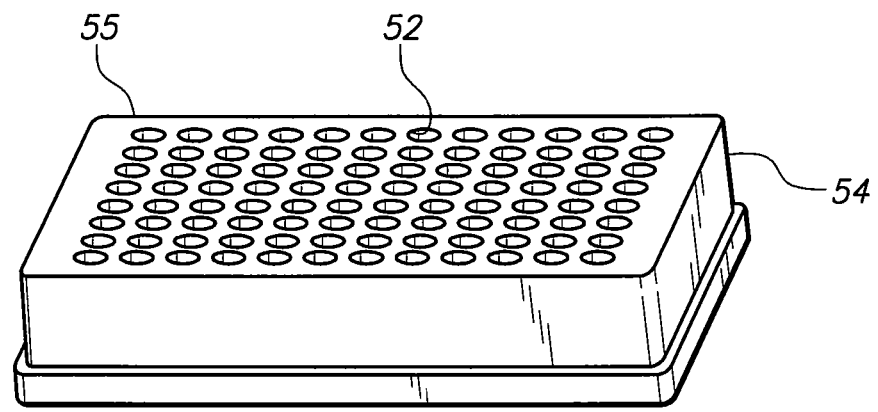
FIG. 5 is a perspective view of a receiving member for use in processing plant samples in accordance with the present invention.

In essence, the transfer process of the present invention involves the transfer of plant material from individual storage locations 40 of a magazine 38 into respective wells 52 of a receiving member 54. As seen in FIG. 5, the receiving member 54 that is used for the transfer is a tray and includes a plurality of wells 52 (e.g. ninety six wells). The wells 52 are typically arranged in a rectangular array with labeled rows and columns. Further, one corner of the tray 54 is typically identified as the origin so that the wells 52 on the tray 54 can be distinguished from one another. For purposes of the present invention, the tray 54 includes a discrete feature 55 which allows the identification of each specific well 52. Specifically, the discrete feature 55 allows identification of the receiving member 54 and the origin and arrangement of the wells 52 serve as a key for determining the location of a particular well 52 on the receiving member 54.

Cross referencing FIGS. 1, 4 and 5, the transfer of plant material may be understood. In the transfer of plant material from a storage location 40 to a well 52, the integrity of the plant material in the storage location 40 must be maintained, i.e., there should be no cross-contamination between samples. Further, according to the work-list 26, the identification of the transferred plant material (according to the respective unique feature(s) 22) must also be maintained. In detail, this information is documented and preserved as an output report 56 that collates information from the unique features 22, from the magazines 38 and from the trays 54. Consequently, the plant material in each particular well 52 of each tray 54 can be traced back to its plant 20 of origin.

Referring back to FIG. 1, it is noted that the system 10 is provided with a mechanism to prevent sampling mistakes. As a result, the system 10 maintains the traceability of plant samples in a fault tolerant manner. Specifically, a code can be entered into the keypad 36 to instruct the controller 12 to label samples in certain storage locations 40 as being mistakes. As a result, during the transfer process from a magazine 38 to a tray 54, the storage locations 40 holding samples which have been identified as mistakes are not transferred to the trays 54.

OPERATION

In the operation of the present invention, an experiment is planned and a plant database 14 including virtual identifications for a desired number of plants 20 is prepared. In the field 18 or greenhouse, a selected number of seeds, grafts or plants are planted. Thereafter, the sprouted seeds or plants 20 are identified in relation to the database 14. Specifically, as a user proceeds through the field 18, he/she creates a unique feature 22 and applies it to a plant 20. For instance, the unique feature 22 may be placed directly on the plant 20 or on a stake 24 positioned near the plant 20. Alternatively, the GPS coordinates of the plant 20 may be identified. As each plant 20 is identified by a unique feature 22, or by the plant's position relative to a unique feature 22, the plant 20 is tied to a virtual plant in the database 14. After a plant 20 is matched with an identity, the location of the now identified plant 20 is installed in the controller 12.

Thereafter, the user can take samples of plant material from the plant 20, using the sampling device 28. In this process, the identity of the plant 20 is ascertained when the retrieving unit 29 reads the unique feature 22. Further, the identity of the magazine 38 receiving the plant sample is also determined by reading its distinct feature 39. Then, leaf plugs (i.e. plant material) are deposited into or onto a storage location 40 of the magazine 38. For certain operations, the material from only one plant 20 is collected into a particular storage location 40 and there is no mixing of plant material at the storage location 40. In other operations, such as bulking procedures, material from multiple plants 20 is collected at a storage location 40, i.e., plant material is intentionally mixed at the storage location 40. When a desired amount of samples have been received in a magazine 38, the magazine 38 is removed from the sampling device 28 and replaced with another magazine 38. This continues until all selected plants 20 in a field 18 have been sampled. Note, this may require all plants 20 be sampled, or it may require the sampling of only representative plants 20. In order to trace the source of each sample, the handheld computer 31 logs all sampling data and communicates the sampling data to the controller 12.

After the magazines 38 have been filled, they are bundled and sent for transfer (see transfer station 50). After they have been transferred, the plant material is processed to extract DNA from the material. This DNA is then processed to assess genetic markers for further use.

EXAMPLE

In order to further explain the present invention, an example is provided. In the Example, an experiment (labeled EXAM) is planned for analyzing certain genetic features in the progeny of two plants. It is determined that the experiment requires samples from one hundred plants, including ten from each parent and eighty from the progeny. Therefore, a database 14 is created with virtual identifications for plants labeled EXAM-001 through EXAM-100. Further, the database 14 includes instructions that the parent plants be numbered EXAM-081 through EXAM-100.

In order to ensure that a sufficient number of progeny are grown, one hundred and fifty progeny seeds are planted. During planting, the seeds are located in six rows of twenty-five. Also, each pair of ten genetically-identical parent plants are planted in two defined rows. After the progeny seeds sprout into viable plants, the plant labeling process takes place. Specifically, beginning at a known location relative to the plants 20 (for instance, the north east corner of the array of plants 20), a user attaches a unique feature 22 to every fifth plant. The user follows a set pattern, such as north-to-south through each row and east-to-west from row to row. Once sufficient unique features 22 for eighty progeny and twenty parent plants have been applied, the labeling process is finished. With the completion of the labeling process, each plant 20 to be tested has been matched with one of the virtual identifications in the database 14.

Thereafter, plant samples may be taken from the plants 20. Specifically, the user uses the plant sampling device 28 to read the distinct feature 39 on a magazine 38, and then connects the magazine 38 to the sampling device 28. The sampling device 28 automatically locates the register 42 within the magazine 38 and is prepared to insert a plant sample at the first storage location 40. Thereafter, the user identifies the first plant 20, by using the sampling device 28 to read the unique feature 22 at the plant 20. Then, the user operates the keypad 36 on the sampling device 28 to take from the plant 20 the desired number of samples. After the desired samples from the first plant 20 have been taken, the user instructs the sampling device 28 that the adjacent plant 20 will be sampled. This process is repeated until the next plant 20 having a unique feature 22 is encountered. Then the sampling device 28 is used to read the unique feature 22, as was done with the first plant 20.

As the unique features 22 are read, the user ensures that the number of plants 20 believed to be sampled and the actual number of samples taken according to the sampling device 28 are the same. For instance, in this example, when using the plant sampling device 28 to read the unique feature 22 at the sixteenth plant, the user notices that the plant sampling device 28 has already recorded taking sixteen samples. Because sampling at the eleventh plant did not display this error, the user knows that a mistake was made between the eleventh and sixteenth plants 20. In order to correct the error, the user enters a mistake code into the plant sampling device 28 and returns to the eleventh plant. The unique feature 22 at the eleventh plant is read and a sample is taken. Then, the user proceeds with the typical sampling process.

When a desired number of samples have been received in the magazine 38, the user disconnects that magazine 38, reads the distinct feature 39 from a replacement magazine 38 and connects the replacement magazine 38 to the plant sampling device 28. Again, the sampling device 28 automatically finds the register 42 within the magazine 38 and positions the first storage location 40 to receive a sample.

When the sampling process is finished, the magazines 38 are carried to a transfer station 50. Also, the sampling data is communicated to the controller 12 by the handheld computer 31. At the transfer station 50, the work-list 26 for the invention is read and the transfer instructions are performed. For instance, the work-list 26 may require that one sample from each parent plant and ten samples from the progeny be positioned in specific wells 52 on ten trays 54. Thereafter, each magazine 38 is sequentially identified and connected to the transfer station 50. Further, each tray 54 is connected to the transfer station 50 and is identified by the transfer station 50. For each magazine 38, the controller 12 identifies the source plant 20 for the sample at each storage location 40 based on the data received from the handheld computer 31. According to the work-list 26, the transfer station 50 transfers each sample to a selected well 52 in a selected tray 54. Thereafter, the plant source for any sample can be identified by identifying the well 52 and tray 54 in which the sample is located. With the well 52 and tray 54 known, the storage location 40 and magazine 38 are known, thus the plant 20 from which the sample came is known.

As noted above, the controller 12 has identified the storage locations 40 that include sampling mistakes. Therefore, those storage locations 40 are not transferred to the trays 54.

While the particular System for Sampling and Tracking Plant Material as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A magazine system for sampling plant tissue system comprising:
    (a) a sampling device including
        a punch and die mechanism for taking samples at a punch position, and
        an actuator for rotating a drive mechanism of a magazine; and
    (b) a magazine in removable engagement with said sampling device, said magazine including
        (b1) a pathway substantially enclosed within said magazine,
        (b2) a plurality of mobile storage capsules for retaining plant tissue samples, wherein said plurality of mobile storage capsules are positioned in and moveable within said pathway, and
        wherein each of said plurality of mobile storage capsules define an opening for receiving a plant tissue sample,
        (b3) a drive mechanism including
            a first set of teeth for receiving said actuator of said sampling device, and
            a second set of teeth interfaced with said plurality of mobile storage capsules, wherein rotation of said drive mechanism moves said capsules within said pathway, and
        (b4) a punch position located proximate said pathway, wherein said openings of said mobile storage capsules are individually alignable with said punch position by rotation of said drive mechanism.

2. The system according to claim 1, wherein rotation of said magazine's drive mechanism sequentially engages said plurality of mobile storage capsules to sequentially convey said plurality of mobile storage capsules along the pathway and to the punch position.

3. The system according to claim 1, wherein said drive mechanism is mounted, at least in part, within said magazine and adjacent to at least a part of said pathway.

4. The system according to claim 1, wherein said plurality of mobile storage capsules are shaped to be received by said second set of teeth of said drive mechanism.

5. The system according to claim 1, further comprising a register storage location moveably positioned within said pathway,
    wherein actuation of said drive mechanism moves said register storage location within said pathway, and
    wherein the identity of any of said plurality of mobile storage capsules is determinable relative to the register location.

6. The system according to claim 1, further comprising a plant sample within at least one of said plurality of mobile storage capsules.

7. The system according to claim 1, further comprising a counter for determining the position of each storage location relative to the register.

* * * * *